(12) United States Patent
Qin et al.

(10) Patent No.: US 8,269,060 B2
(45) Date of Patent: Sep. 18, 2012

(54) ABSORBENT MATERIALS AND ABSORBENT ARTICLES INCORPORATING SUCH ABSORBENT MATERIALS

(75) Inventors: Jian Qin, Appleton, WI (US); Xiaomin Zhang, Appleton, WI (US); Debra Ann Graverson, Appleton, WI (US)

(73) Assignee: Evonik Stockhausen, LLC, Greensboro, NC (US)

( * ) Notice: Subject to any disclaimer, the term of this patent is extended or adjusted under 35 U.S.C. 154(b) by 315 days.

(21) Appl. No.: 12/636,440

(22) Filed: Dec. 11, 2009

(65) Prior Publication Data

US 2010/0114050 A1    May 6, 2010

Related U.S. Application Data

(62) Division of application No. 10/631,916, filed on Jul. 31, 2003, now Pat. No. 7,696,401.

(51) Int. Cl.
*A61F 13/15* (2006.01)
*A61F 13/20* (2006.01)

(52) U.S. Cl. ......... 604/367; 604/368; 604/372; 604/376

(58) Field of Classification Search .................... 522/14, 522/153; 523/201; 525/55; 604/372, 367, 604/368, 376
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,128,692 A | 12/1978 | Reid |
| 4,340,563 A | 7/1982 | Appel et al. |
| 4,777,073 A | 10/1988 | Sheth |
| 4,795,668 A | 1/1989 | Krueger et al. |
| 4,888,238 A | 12/1989 | Katz et al. |
| 5,108,820 A | 4/1992 | Kaneko et al. |
| 5,274,018 A | 12/1993 | Tanaka et al. ............ 524/166 |
| 5,324,561 A | 6/1994 | Rezai et al. |
| 5,336,552 A | 8/1994 | Strack et al. |
| 5,382,400 A | 1/1995 | Pike et al. |
| 5,382,610 A | 1/1995 | Harada et al. |
| 5,451,353 A | 9/1995 | Rezai et al. |
| 5,539,019 A | 7/1996 | Suskind et al. |
| 5,540,992 A | 7/1996 | Marcher et al. |
| 5,618,622 A | 4/1997 | Gillberg-Laforce et al. |
| 5,669,894 A | 9/1997 | Goldman et al. |
| 5,843,575 A | 12/1998 | Wang et al. |
| 5,853,867 A | 12/1998 | Harada et al. |
| 5,883,158 A * | 3/1999 | Nambu et al. ............ 523/412 |
| 6,027,804 A | 2/2000 | Chou et al. |
| 6,068,924 A | 5/2000 | Palumbo |
| 6,162,541 A | 12/2000 | Chou et al. |
| 6,239,230 B1 | 5/2001 | Eckert et al. |
| 6,258,996 B1 | 7/2001 | Goldman |
| 6,270,893 B1 | 8/2001 | Young, Sr. et al. |
| 6,376,618 B1 | 4/2002 | Mitchell et al. |
| 6,380,456 B1 | 4/2002 | Goldman |
| 6,387,495 B1 | 5/2002 | Reeves et al. |
| 6,391,451 B1 | 5/2002 | Mitchell et al. |
| 6,509,512 B1 * | 1/2003 | Beihoffer et al. ............ 604/372 |
| 7,098,284 B2 | 8/2006 | Torii et al. |
| 2006/0229413 A1 | 10/2006 | Torii et al. |
| 2008/0058747 A1 | 3/2008 | Singh Kainth et al. ....... 604/368 |

FOREIGN PATENT DOCUMENTS

| | | |
|---|---|---|
| CA | 2433044 | 7/2002 |
| EP | 493011 A2 | 12/1991 |
| EP | 763364 A2 | 9/1996 |
| JP | 2000-095955 | 7/1999 |
| JP | 2000-095955 * | 4/2000 |
| JP | 2001295193 A | 10/2001 |
| WO | WO 95/22356 A1 | 8/1995 |
| WO | WO 96/15163 * | 5/1996 |
| WO | WO 96/17681 A1 | 6/1996 |
| WO | 9847454 | 10/1998 |
| WO | WO 99/25393 * | 5/1999 |
| WO | WO 01/77437 A1 | 10/2001 |
| WO | 02053199 | 7/2002 |
| WO | 02059214 A1 | 8/2002 |
| WO | WO 03/043670 A1 | 5/2003 |
| WO | WO 03/052206 A1 | 6/2003 |
| WO | WO 2004/061235 A1 | 7/2004 |
| WO | WO 2004/069915 A2 | 8/2004 |

* cited by examiner

OTHER PUBLICATIONS

International Search Report for PCT/US2004/010205 dated Nov. 11, 2004, 4 pages.

*Primary Examiner* — Ling Choi

*Assistant Examiner* — Monique Peets

(74) *Attorney, Agent, or Firm* — Smith Moore Leatherwood LLP; Philip P. McCann

(57) ABSTRACT

An absorbent material formed at least in part of a crosslinked polymer. The absorbent material has a centrifuge retention capacity as determined by a Centrifuge Retention Capacity Test of at least about 20 g/g and a gel bed permeability under load as determined by a Gel Bed Permeability Under Load Test of at least about $300 \times 10^{-9}$ cm$^2$ or a free swell gel bed permeability as determined by a Free Swell Gel Bed Permeability Test of at least about $2,500 \times 10^{-9}$ cm$^2$. The crosslinked polymer may comprise either at least about 75 weight percent anionic polymer or at least about 75 weight percent cationic polymer. In one embodiment, the cross-linked polymer is surface treated with a water soluble non-cross-linked polymer having a potential for becoming charged opposite that of the cross-linked polymer.

7 Claims, 2 Drawing Sheets

ABSORBENT MATERIALS AND ABSORBENT ARTICLES INCORPORATING SUCH ABSORBENT MATERIALS

This application is a divisional of U.S. application Ser. No. 10/631,916, filed on Jul. 31, 2003, now U.S. Pat. No. 7,696,401, for Absorbent Materials And Absorbent Articles Incorporating Such Absorbent Materials, the disclosure of which is expressly incorporated herein by reference.

BACKGROUND OF THE INVENTION

This invention relates generally to absorbent materials such as those used in making absorbent structures for disposable articles including diapers, children's training pants, feminine care articles, incontinence articles, bandages, surgical gowns, absorbent wipes and the like, and more particularly to such absorbent materials having an enhanced gel bed permeability under load.

Conventional disposable articles typically include an absorbent structure, also sometimes referred to as an absorbent core or absorbent composite, formed by air-forming, air-laying, co-forming, wet-laying or other known forming technique. There is a continuing effort by absorbent structure manufacturers to improve the liquid intake performance of absorbent structures to thereby reduce the tendency of such a structure to leak as it becomes increasingly saturated during use, particularly where the structure is subjected to repeated liquid insults before being discarded. For example, one means of reducing the leakage of absorbent structures has been the extensive use of superabsorbent materials. In addition to increasing the amount of superabsorbent material mass, recent efforts in commercial absorbent structure design have generally focused on using a higher concentration of superabsorbent material and less fiber to make the absorbent structure thinner and denser.

However, notwithstanding the increase in total absorbent capacity obtained by increasing the concentration of superabsorbent material, such absorbent structures may still leak during use. The leakage may in part be the result of the structure having an insufficient intake rate, e.g., the rate at which a liquid insult can be taken into and entrained within the structure for subsequent absorption by the superabsorbent material. More particularly, the intake rate of such absorbent structures may decrease upon repeated insults thereof due to the tendency of the superabsorbent material within the structure to swell as it absorbs and thus restrict or otherwise block the open channels between superabsorbent particles, or between the particles and the hydrophilic fibers within the absorbent structure. This phenomenon is often referred to as a form of gel-blocking and may occur as a result of the superabsorbent material lacking sufficient gel integrity under an external pressure, such as those loads applied by a wearer during movement or upon sitting down.

The ability to maintain openness of and accessibility to channels and void volume within an absorbent structure may in large part be a function of the gel bed permeability (GBP) under load of the superabsorbent material in the structure. A higher GBP under load indicates a higher ability to maintain open channels within the absorbent structure as the superabsorbent material swells under loads such as those encountered during use.

There is a need, therefore, for absorbent structures incorporating absorbent materials which have a relatively high absorbency and an enhanced free swell gel bed permeability (GBP) and gel bed permeability under load.

SUMMARY OF THE INVENTION

In one embodiment, an absorbent material of the present invention generally comprises at least in part a cross-linked polymer. The absorbent material has a centrifuge retention capacity as determined by a Centrifuge Retention Capacity Test of at least about 20 g/g and a gel bed permeability under load as determined by a Gel Bed Permeability Under Load Test of at least about $300 \times 10^{-9}$ cm$^2$.

In another embodiment, an absorbent material of the present invention generally comprises at least in part a cross-linked polymer. The absorbent material has a centrifuge retention capacity as determined by a Centrifuge Retention Capacity Test of at least about 20 g/g and a free swell gel bed permeability as determined by a Free Swell Gel Bed Permeability Test of at least about $2,500 \times 10^{-9}$ cm$^2$.

A surface treated absorbent material according to one embodiment of the present invention generally comprises a superabsorbent material having a gel stiffness index of at least about 0.8. The superabsorbent material comprises a cross-linked polymer comprising at least about 75 weight percent anionic polymer. A surface treatment is applied to the superabsorbent material and comprises a water soluble non-cross-linked polymer comprising at least about 50 weight percent cationic polymer.

In another embodiment, the surface treated absorbent material comprises a superabsorbent material having a gel stiffness index of at least about 0.8. The superabsorbent material comprises a cross-linked polymer comprising at least about 75 percent by weight cationic polymer. A surface treatment is applied to the superabsorbent material and comprises a water soluble noncross-linked polymer comprising at least about 50 percent by weight anionic polymer.

In general, one embodiment of a method of making a surface treated absorbent material generally comprises solubilizing a water soluble cationic polymer in water to form an aqueous solution. The solution is applied to the outer surface of a superabsorbent material having a gel stiffness index of at least about 0.8 and comprising a cross-linked polymer comprising at least about 75 weight percent anionic polymer.

In another embodiment, a method of making a surface treated absorbent material generally comprises solubilizing a water soluble anionic polymer in water to form an aqueous solution. The solution is applied to the outer surface of a superabsorbent material having a gel stiffness index of at least about 0.8 and comprising a cross-linked polymer comprising at least about 75 weight percent cationic polymer.

Other features of the invention will be in part apparent and in part pointed out hereinafter.

DEFINITIONS

Within the context of this specification, each term or phrase below will include the following meaning or meanings:

"Bi-component," or "Multi-component" fibers as used herein refers to fibers formed from two (e.g., bicomponent) or more components, such as a natural fiber and a polymer or two or more polymers extruded from separate extruders, joined together to form a single fiber. The components are arranged in substantially constantly positioned distinct zones across a cross-section of the multi-component fibers and extend continuously along at least a portion of, and more desirably the entire, length of the fiber. The configuration of the multi-component fibers may be, for example, a sheath/ core arrangement in which one polymer is surrounded by another, a side-by-side arrangement, a pie arrangement, an "islands-in-the-sea" arrangement or other suitable arrangement. Bi-component fibers are disclosed in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Bi-component fibers are also taught in U.S. Pat. No. 5,382,400 to Pike et al. and may be used to produce crimp in the fibers by using the differential rates of expansion and contraction of the two (or more) polymers.

II Bonded-Carded" refers to webs that are made from staple length fibers which are sent through a combing or carding unit, which separates or breaks apart and aligns the fibers in the machine direction to form a generally machine direction-oriented fibrous non-woven web. This material may be bonded together by methods that include point bonding, through air bonding, ultrasonic bonding, adhesive bonding or other suitable bonding technique.

"Hydrophilic" describes a material or surface which is wetted by aqueous liquids in contact therewith. The degree of wetting can, in turn, be described in terms of the contact angles and the surface tensions of the liquids and materials involved. Equipment and techniques suitable for measuring the wettability of particular materials or surfaces can be provided by a Cahn SFA-222 Surface Force Analyzer System, or a substantially equivalent system. When measured with this system, materials or surfaces having contact angles less than 90 degrees are designated "wettable" or hydrophilic, and those having contact angles greater than 90 degrees are designated "nonwettable" or hydrophobic.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are typically microfibers which may be continuous or discontinuous, are generally about 0.6 denier or smaller, and are generally self bonding when deposited onto a collecting surface.

"Non-woven" or "non-woven web" refers to materials or webs that are formed without the aid of a textile weaving or knitting process. Non-woven structures have been formed from many processes such as, for example, meltblowing processes, spunbonding processes, and bonded carded processes.

"Spunbond" refers to small diameter fibers which are formed by extruding molten thermoplastic material as filaments from a plurality of fine capillaries of a spinneret having a circular or other configuration, with the diameter of the extruded filaments then being rapidly reduced by an air-drawing process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers of about 0.3 or larger, more particularly, between about 0.6 and about 10.

"Superabsorbent" and "Superabsorbent Material" refer to a water-swellable, water-insoluble organic or inorganic material capable, under the most favorable conditions, of absorbing at least about 10 times its weight and, more suitably, at least about 20 times its weight in an aqueous solution containing 0.9 weight percent sodium chloride solution in water.

"Thermoplastic" describes a material that softens when exposed to heat and which substantially returns to a non-softened condition when cooled to room temperature.

DETAILED DESCRIPTION

Figure 1:
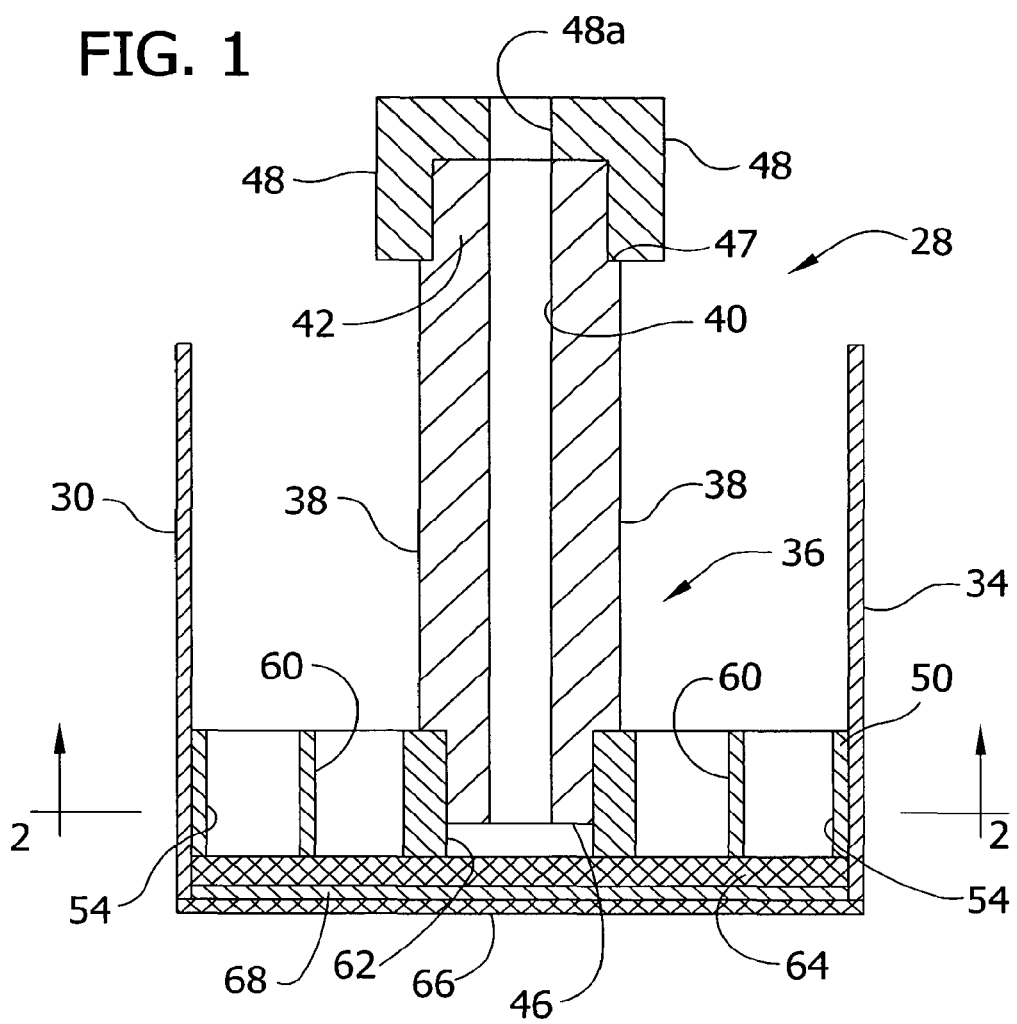
FIG. 1 is a cross-section of apparatus for conducting a Gel Bed Permeability Test.

The present invention is directed generally to surface treated absorbent materials having enhanced liquid handling properties, and more particularly to absorbent materials having a high gel absorbency and an enhanced gel bed permeability under load. The present invention is also directed to absorbent structures containing such surface treated absorbent materials and to absorbent articles incorporating these absorbent structures. For example, such absorbent articles include, without limitation, feminine care pads, interlabial products, tampons, diapers, incontinence articles such as pads, guards, pants and undergarments, training pants, medical garments, bed pads, sweat absorbing pads, shoe pads, bandages, helmet liners, wipes, etc. As another example, the absorbent structure may be useful by itself, such as in the form of a tissue, towel, napkin or the like.

In accordance with one embodiment of the present invention, the surface treated absorbent material generally comprises a superabsorbent material and a surface treatment applied to the outer surface of the superabsorbent material. Suitable superabsorbent materials may be selected from natural, biodegradable, synthetic and modified natural polymers and materials. In addition, the superabsorbent materials can be inorganic materials, such as silica gels, or organic compounds such as cross-linked polymers. The term "cross-linked" as used in reference to the superabsorbent material refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces. It is understood that the cross-linking includes surface cross-linking and/or bulk cross-linking.

In one particular embodiment, the superabsorbent material comprises a cross-linked polymer comprising at least about 75 weight percent anionic polymer. The term polymer as used herein is intended to refer to either a single polymer or to a mixture of polymers. The term "anionic polymer" is intended to refer to a polymer or mixture of polymers comprising a functional group or groups having a potential for becoming negatively charged ions upon ionization in an aqueous solution. More suitably, the superabsorbent material comprises a cross-linked polymer comprising at least about 85 weight percent anionic polymer, and even more suitably at least about 90 weight percent anionic polymer. In general, suitable functional groups for an anionic polymer include, but are not limited to, carboxyl groups, sulfonate groups, sulphate groups, sulfite groups, and phosphate groups.

Suitably, the functional groups are carboxyl groups. It is preferred that these functional groups are in neutralized form. A suitable degree of neutralization is at least 50%, more suitably at least 60%, and even more suitably at least 70%.

Examples of synthetic anionic polymers include the alkali metal and ammonium salts or partial salts of poly(acrylic acid), poly(methacrylic acid), hydrolyzed poly (acrylamides), maleic anhydride copolymers with vinyl ethers and alpha-olefins, poly(vinyl acetic acid), poly(vinyl sulfonic acid), poly(vinyl phosphonic acid), poly(vinyl ethers), poly (vinyl pyrrolidone), poly(vinylmorpholinone), poly(vinyl alcohol), and mixtures and copolymers thereof. Examples of natural based anionic polymers include the salts or partial salts of carboxymethyl cellulose, carboxymethyl starch, alginates, and carrageenans. Other suitable examples of anionic polymers include synthetic polypeptides such as polyaspartic acid and polyglutamic acid.

In another embodiment, the superabsorbent material comprises a cross-linked polymer comprising at least about 75 weight percent cationic polymer. A cationic polymer as used herein refers to a polymer or mixture of polymers comprising a functional group or groups having a potential of becoming positively charged ions upon ionization in an aqueous solution. More suitably, the superabsorbent material comprises a cross-linked polymer comprising at least about 85 weight percent cationic polymer, and even more suitably at least about 90 weight percent cationic polymer. In general, suitable functional groups for a cationic polymer include, but are not limited to, primary, secondary, or tertiary amino groups, imino groups, imido groups, amido groups, and quaternary ammonium groups. It is preferred that these functional groups are in neutralized form. A suitable degree of neutralization is at least 50%, more suitably at least 60%, and even more suitably at least 70%.

Examples of synthetic cationic polymers include the salts or partial salts of poly{vinyl amines), poly (allylamines), poly(ethylene imine), poly(amino propanol vinyl ethers), poly(acrylamidopropyl trimethyl ammonium chloride), poly{diallyldimethyl ammonium chloride). Examples of natural based cationic polymers include partially deacetylated chitin, chitosan and chitosan salts. Also synthetic polypeptides such as polyasparagins, polylysines, polyglutamines, polyarginines can be examples of the cationic polymers.

In one embodiment, the superabsorbent material useful for making the surface treated absorbent material is in the form of discrete particles. Superabsorbent material particles can be of any suitable shape, for example, spiral or semi-spiral, cubic, rod-like, polyhedral, etc. Particle shapes such as needles, flakes, films and fibers are also contemplated for use herein. Conglomerates of particles of superabsorbent material may also be used. The superabsorbent materials may also be of various length and cross-sectional dimensions.

In accordance with the present invention, the superabsorbent materials suitable for making the surface treated absorbent materials have certain liquid handling characteristics, including a gel stiffness index which is suitably at least about 0.8, more suitably at least about 0.85, even more suitably at least about 0.90, and still more suitably at least about 0.95. The gel stiffness index of a superabsorbent material generally refers to the ability of the material to resist deformation under load and is particularly defined herein as the absorbency under load value (AUL) of the superabsorbent material as determined by an Absorbency Under Load Test conducted at a load of about 0.9 psi, divided by the centrifuge retention capacity (CRC) of the superabsorbent material as determined by a Centrifuge Retention Capacity Test. The Absorbency Under Load Test and the Centrifuge Capacity Test are set forth later herein.

In one particular embodiment, the superabsorbent material with the surface treatment of the present invention suitably has a centrifuge retention capacity (CRC) as determined by the Centrifuge Retention Capacity Test of at least about 20 grams liquid per gram weight of superabsorbent material, more suitably at least about 23 grams liquid per gram weight of superabsorbent material, still more suitably about 25 grams liquid per gram weight of superabsorbent material and even more suitably at least about 28 grams liquid per gram weight of superabsorbent material.

As an example, one suitable superabsorbent material is made by Stockhausen, Inc. of Greensboro, N.C., U.S.A., under the designation SXM 9543. This superabsorbent material is a cross-linked sodium polyacrylate based (anionic) polymer and has an AUL at 0.9 psi (6.2 kPa) as determined by the AUL Test of about 21.6 gig and a CRC as determined by the CRC Test of about 23.2 gig. The gel stiffness index of such a superabsorbent material is therefore about 0.93.

The surface treatment of the surface treated absorbent material comprises at least in part a water soluble non-cross-linked polymer applied to all or part of the outer surface of the superabsorbent material and having a potential for becoming charged opposite that of the superabsorbent material. For example, where the superabsorbent material comprises a cross-linked polymer that is generally anionic (e.g., comprises at least about 75% by weight anionic polymer), so as to have a potential for becoming negatively charged, the surface treatment at least in part comprises a water-soluble non-cross-linked polymer comprising a cationic polymer, which has potential for becoming positively charged. More particularly, the non-cross-linked polymer comprises at least about 50% by weight cationic polymer, more suitably at least about 60% by weight cationic polymer, still more suitably at least about 70% by weight cationic polymer and even more suitably at least about 80% by weight cationic polymer. The cationic polymer is suitably non-crosslinked and water soluble for reasons which will become apparent.

Examples of suitable synthetic cationic polymers for use as the surface treatment include the salts or partial salts of poly (vinyl amines), poly (allylamines), poly(ethylene imine), poly(amino propanol vinyl ethers), poly(acrylamidopropyl trimethyl ammonium chloride), poly(diallyldimethyl ammonium chloride). Examples of suitable natural based cationic polymers include partially deacetylated chitin, chitosan and chitosan salts. Synthetic polypeptides such as polyaspara-gins, polylysines, polyglutamines, polyarginines are additional examples of suitable cationic polymers.

Examples of suitable synthetic anionic polymers for use as the surface treatment include the salts or partial salts of polyacrylic acid, polymethacrylic acid, maleic anhydride copolymer, polyvinyl acetic acid, polyvinyl phosphonic acid, and polyvinyl sulfonic acid. Examples of suitable natural based anionic polymers include carboxymethyl cellulose, carboxymethyl starch, carrageenan, alginic acid, and alginate. Synthetic polypeptides such as polyaspartic acid, polyglutamic acid, and polysuccinic acid are additional examples of suitable anionic polymers.

Where the superabsorbent material comprises a cross-linked polymer that is generally cationic (e.g., comprises at least about 75% by weight cationic polymer), the surface treatment suitably at least in part comprises a water soluble non-cross-linked polymer comprising an anionic polymer.

More particularly, the non-cross-linked polymer comprises at least about 50% by weight anionic polymer, more suitably at least about 60% by weight anionic polymer, still more suitably at least about 70% by weight anionic polymer and even more suitably at least about 80% by weight anionic polymer. The anionic polymer is suitably non-crosslinked and water-soluble for reasons which will become apparent.

The concentration of surface treatment polymer on the superabsorbent material is suitably in the range of about 0.05 to about 10 percent by weight of the superabsorbent material, and more suitably in the range of about 0.5 to about 5 percent by weight of the superabsorbent material.

The surface treatment may further comprise a solubilizing agent, such as water (and more particularly distilled water), in which the surface treatment polymer is solubilized for ease of applying the surface treatment to the superabsorbent material and to provide a relatively low initial amount of swelling of the superabsorbent material. Upon solubilizing the surface treatment polymer in water, the surface treatment becomes an aqueous solution.

In accordance with one method of making the surface treated absorbent material, the surface treatment polymer is applied to a superabsorbent material having the potential of becoming charged opposite that of the surface treatment polymer. It is also contemplated that the superabsorbent material to which the surface treatment polymer is applied may further have a gel stiffness index of at least about 0.8 without departing from the scope of this invention. In a particular embodiment, an aqueous solution is prepared by solubilizing the surface treatment polymer in water, and more suitably in distilled water.

The amount of water in which the surface treatment polymer is solubilized depends generally on a desired "swell ratio" of the superabsorbent material upon application of the aqueous surface treatment to the superabsorbent material and also upon the desired concentration of surface treatment polymer to remain on the superabsorbent material. As used herein, the swell ratio is defined as the amount of water (by weight) in the aqueous surface treatment per one gram weight of superabsorbent material to which the surface treatment is to be applied. A higher swell ratio promotes deep penetration of the surface treatment polymer into the superabsorbent material. However, a relatively higher swell ratio may be needed when a high molecular weight surface treatment polymer is used due to a higher potential viscosity. As an example, the swell ratio is suitably in the range of about 0.5 to about 20, more suitably in the range of about 0.5 to about 10, and still more suitably in the range of about 1 to about 5.

As an additional example, assuming that 10 grams of superabsorbent material are to be surface treated so that the surface treatment polymer concentration on the superabsorbent material is approximately 2.5 percent by weight of the superabsorbent material. Thus, the amount of surface treatment polymer needed is 2.5 percent times 10 grams, or 0.25 grams weight of the surface treatment polymer. Further assuming that the desired swell ratio is about 2.5, the required amount of water in which the surface treatment is solubilized is 2.5 times 10 grams, or 25 grams weight of water.

The surface treatment is suitably applied to the superabsorbent material by vigorously mixing (e.g., stirring) the superabsorbent material in the aqueous solution formed by solubilizing the surface treatment polymer. It is understood, however, that the surface treatment may be applied to the superabsorbent material using various other suitable techniques, such as spraying, condensing, coating, etc. and remain within the scope of this invention.

Upon stirring the superabsorbent material in the aqueous solution, water is absorbed by the superabsorbent material along with a small amount of the surface treatment polymer. The treated superabsorbent material is then subjected to a conventional drying operation to remove water remaining on the surface of the superabsorbent material to thereby leave the surface treatment polymer on the surface of the superabsorbent material. The drying operation may be by evaporation, vacuum suction, heat drying, freeze drying, organic solvent coagulation or other suitable removal technique.

Since the superabsorbent material is surface treated with a polymer having a charge potential opposite that of the superabsorbent material, there is no strong ionic attraction between the particles of surface treated absorbent material when the particles are dry or at a low degree of saturation, e.g., prior to the material being insulted and substantially swelled. When the particles are subsequently insulted by liquid, such as urine, the superabsorbent material absorbs the liquid and swells. As a result, the superabsorbent material becomes exposed so that both cationic and anionic regions are present at the surfaces of the particles of surface treated absorbent material.

The cations at the surface of one swollen particle will attract anions at the surface of other swollen particles, and vice versa, thereby enhancing the binding power between particles, e.g., causing the particles to "stick" together. Once this occurs, inter-particle movement is substantially inhibited and, where the gel stiffness index of the superabsorbent material is at least about 0.8, further swelling of the stuck together particles will generate open voids, or air pockets, between particles. Maintaining and/or creating these open voids as the particles swell under pressure, such as due to the wearer sitting, walking, twisting, etc., substantially increases the permeability of the surface treated absorbent material.

As an example, the surface treated absorbent material suitably has a gel bed permeability (GBP) under load as determined by a Gel Bed Permeability Under Load Test set forth later herein of at least about $200 \times 10^{-9}$ cm$^2$, more suitably at least about $250 \times 10^{-9}$ cm$^2$, still more suitably at least about $300 \times 10^{-9}$ cm$^2$, even more suitably at least about $350 \times 10^{-9}$ cm$^2$, still more suitably at least about $400 \times 10^{-9}$ cm$^2$, still more suitably at least about $450 \times 10^{-9}$ cm$^2$, even still more suitably at least about $500 \times 10^{-9}$ cm$^2$, and further more suitably at least about $550 \times 10^{-9}$ cm$^2$.

As an additional example, the surface treated absorbent material suitably has a free swell gel bed permeability (GBP) as determined by a Free Swell Gel Bed Permeability Test set forth later herein of at least about $2,000 \times 10^{-9}$ cm$^2$, more suitably at least about $2,500 \times 10^{-9}$ cm$^2$, and still more suitably at least about $3,000 \times 10^{-9}$ cm$^2$.

EXPERIMENT 1

Three commercially available superabsorbent materials were each subjected to the Centrifuge Retention Capacity (CRC) Test, Absorbency Under Load (AUL) Test, a free swell Gel Bed Permeability (GBP) Test and a Gel Bed Permeability (GBP) Under Load Test as described later herein. Two of the tested superabsorbent materials are commercially available from Stockhausen, Inc. of Greensboro, N.C., U.S.A. as model designations Favor 880 and SXM 9543, respectively. The other tested superabsorbent material is commercially available from Dow Chemical of Midland, Mich., U.S.A. as model designation Dry tech 2035. The test results are reported in Table 1 below.

| Property | Superabsorbent Material | | |
|---|---|---|---|
| | SXM 9543 | Favor 880 | 2035 |
| CRC (g/g) | 23.2 | 31.9 | 27.9 |
| AUL @ 0.9 psi (g/g) | 21.6 | 21.3 | 17.8 |
| Gel Stiffness Index (AUL/CRC) | 0.93 | 0.67 | 0.64 |
| GBP @ 0 psi load ($\times 10^{-9}$ cm$^2$) | 316 | 33.7 | 27.0 |
| GBP @ 0.3 psi load ($\times 10^{-9}$ cm$^2$) | 145 | 9.4 | 6.0 |

Notably, the gel stiffness index for each of the Favor 880 and Dow 2035 superabsorbent materials is less than 0.8 while the gel stiffness index of the SXM 9543 superabsorbent material is suitably greater than about 0.8, and is more particularly about 0.93.

Surface treated absorbent materials were then made by applying a surface treatment to each of the three different superabsorbent materials. More particularly, an aqueous solution comprising distilled water and a solution available from BASF of Charlotte, N.C., under model designation CATIOFAST PR8106 with water was prepared in a 100 ml beaker. CATIOFAST PR8106 is an aqueous solution containing 25 percent by weight polyvinyl amine (which is a cationic polymer) in water. The respective amounts of CATIOFAST PR8106 and the amount of distilled water were based on treating 30 grams weight of dry superabsorbent material and depended on the target concentration of polyvinyl amine polymer to be applied to the superabsorbent material as well as the target swell ratio.

As an example, for a desired polyvinyl amine (surface treatment polymer) concentration of about 2.5 percent by weight of the superabsorbent material, approximately 0.75 grams weight of polyvinyl amine was needed. Since the CATIOFAST PR8106 comprises 25 percent by weight polyvinyl amine in water, the amount of CATIOFAST PR8106 added to the beaker was approximately 3 grams weight (e.g., 0.75 grams of which was polyvinyl amine and 2.25 grams of which was water). For a desired swell ratio of about 2.5, the aqueous solution formed in the beaker included approximately 75 grams weight of water. Since the CATIOFAST PR8106 already included 2.25 grams weight of water, an additional 72.75 grams weight of distilled water was added to the beaker and the mixture was stirred to form the aqueous solution.

Thirty grams of dry superabsorbent material to be treated was then added to the beaker and stirred vigorously by hand therein until all of the aqueous solution was absorbed. The treated superabsorbent material was placed in a 8 inch by 10 inch pan then dried at 60 degrees Celsius in a Baxter Constant Temperature Oven (Model: DK-63), available from Baxter Scientific Products Division, McGaw Park, Ill., for at least 15 hours and then ground into particles by an Osterizer blender at low speed for 10 seconds. The superabsorbent particles obtained were then sieved and 300 to 600 micron cut was used for absorbency related evaluation. The surface treated absorbent materials were each subjected to the CRC Test, the AUL Test at 0.9 psi, the free swell GBP Test and the GBP Under Load Test set forth later herein. The results of the tests performed are provided in Table 2.

| Super-absorbent Material (SAM) | Polyvinyl Amine Conc. Wt. % of SAM) | Swell Ratio | CRC (g/g) | Aul @ 0.9 psi (g/g) | Gel Stiffness Index | Free Swell GBP @ 0 psi ($\times 10^{-9}$ cm$^2$) | GPB under load @ 0.3 psi ($\times 10^{-9}$ cm$^2$) |
|---|---|---|---|---|---|---|---|
| SXM 9543 | 0 | 0 | 23.2 | 21.6 | 0.93 | 316 | 145 |
| | 0 | 2.5 | 24.3 | 21.7 | 0.89 | 176 | 69 |
| | 0.63 | 2.5 | 22.5 | 21.3 | 0.97 | 2365 | 310 |
| | 1.25 | 2.5 | 22.4 | 21.3 | 0.98 | 2880 | 292 |
| | 2.5 | 1.25 | 23.5 | 18.3 | 0.78 | 2452 | 131 |
| | 2.5 | 2.5 | 20.8 | 19.4 | 0.96 | 2799 | 437 |
| | 2.5 | 5 | 23.7 | 19.7 | 0.83 | 2285 | 307 |
| | 5 | 2.5 | 20.0 | 19.4 | 0.99 | 3153 | 269 |
| | 10 | 2.5 | 23.4 | 17.0 | 0.73 | 812 | 77 |
| | 10 | 5 | 19.8 | 10.7 | 0.54 | 1512 | 42 |
| SXM 880 | 0 | 0 | 31.9 | 21.3 | 0.67 | 33.7 | 9.4 |
| | 1.2 | 5 | 30.7 | 9.2 | 0.30 | 31.7 | 2.1 |
| | 2.5 | 10 | 30.4 | 11.8 | 0.39 | 96.9 | 6.2 |
| | 2.5 | 5 | 30.6 | 12.0 | 0.39 | 193.1 | 7.1 |
| | 5 | | 29.8 | 10.0 | 0.34 | 248.3 | 3.1 |
| | 5 | 2.5 | 30.1 | 9.0 | 0.30 | 445.5 | 1.9 |
| | 10 | 2.5 | 30.5 | 6.7 | 0.22 | 286.1 | 0.2 |
| 2035 | 0 | 0 | 27.9 | 17.8 | 0.64 | 27.0 | 6.0 |
| | 2.5 | 2.5 | 25.2 | 18.3 | 0.73 | 1470 | 77 |
| | 5 | 2.5 | 25.4 | 14.8 | 0.58 | 1045 | 109 |
| | 10 | 2.5 | 23.6 | 11.1 | 0.47 | 1530 | 39 |

For the Favor 880 superabsorbent material, which has a gel stiffness index of less than 0.8, applying a surface treatment having a potential for becoming charged opposite that of the superabsorbent material increased the free swell gel bed permeability (e.g., GBP at 0 psi) of the surface treated absorbent material but had little effect on the gel bed permeability under load (e.g., GBP at 0.3 psi) of the surface treated absorbent material. The gel bed permeability under load of the surface treated Dow 2035 superabsorbent material, which also has a gel stiffness index of less than 0.8, was measurably increased, but not as much as desired. However, applying the surface treatment to the SXM 9543 superabsorbent material, which has a gel stiffness of about 0.93, substantially increased both the free swell GBP and the GBP under load of the surface treated absorbent material.

However, the gel bed permeability under load of the treated SXM 9543 tended to be negatively affected by relatively high concentrations of surface treatment. For example, the GBP under load for a polyvinyl amine concentration of about 5 weight percent and a swell ratio of 2.5 was substantially less than the GBP under load for a polyvinyl amine concentration of about 2.5 weight percent and the same swell ratio. This may be because a high surface treatment concentration inhibits swelling of the underlying superabsorbent material, thereby decreasing the absorbency under load (AUL @ 0.9 psi) of the surface treated absorbent material.

It is also noted that the swell ratio should be sufficient to provide adequate distribution of the surface treatment polymer on the superabsorbent material, but is suitably low enough to inhibit excessive penetration of the surface treatment polymer into the superabsorbent material. For example, the GBP under load for a polyvinyl amine concentration of about 2.5 weight percent increased as the swell ratio increased from 1.25 to 2.5, but decreased as the swell ratio was further increased to 5.

EXPERIMENT 2

In another experiment, the SXM 9543 superabsorbent material available from Stockhausen, Inc., without any surface treatment thereon, was subjected to the CRC Test, the AUL Test at 0.9 psi (6.2 kPa), the Free Swell GBP Test and the GBP Under Load Test described later herein. A surface treated absorbent material in accordance with the present invention was then made as follows. 1,210 grams of distilled water was poured into a one gallon Hobart® mixer, model N50 manufactured by Hobart Canada, N.Y., Ontario, Canada and then 54 grams of a solution available from BASF of Charlotte, N.C., under model designation CATIOFAST VFH was added to the mixer while the mixer was stirring at a relatively slow speed (setting 1).

Stirring continued for about 5 minutes or until the CATIOFAST VFH was completely dissolved. CATIOFAST VFH is an aqueous solution containing 22-24 weight percent polyvinyl amine in water. 500 grams of dry SXM 9543 superabsorbent material was added into the solution and stirred vigorously at a relatively fast speed (setting 2) for about 5 minutes. The surface treated absorbent material was placed in two 10 inch by 20 inch pans and dried at 80 degrees Celsius for at least 15 hours in a Baxter oven and then ground by an Osterizer® blender at a low speed for about 10 seconds (about 50 grams of the treated superabsorbent were added into the blender each time). The ground superabsorbent was sieved and 300 to 600 microns particles were used for evaluation. The surface treated absorbent material was then subjected to the CRC Test, the AUL Test at 0.9 psi, the free swell GBP Test and the GBP Under Load Test. The results are provided in Table 3 below.

kenaf; hemp; pineapple leaf fibers; or peat moss. Other hydrophilic fibers, such as regenerated cellulose and curled chemically stiffened cellulose fibers may also be densified to form absorbent structures that can expand to a higher loft when wetted. Pulp fibers may also be stiffened by the use of crosslinking agents such as formaldehyde or its derivatives, glutaraldehyde, epichlorohydrin, methylolated compounds such as urea or urea derivatives, anhydrides such as maleic anhydride, non-methylolated urea derivatives, citric acid or other polycarboxylic acids.

One example of a suitable hydrophilic fiber is commercially available from Bowater of Coosa River, Ala., U.S.A. as model designation CR1654 and is a bleached, highly absorbent sulfate wood pulp containing primarily soft wood fibers. Another suitable hydrophilic fiber is commercially available from Weyerhauser of Federal Way, Wash., U.S.A. as model designation NB-416 and is a bleached southern softwood pulp.

Other examples of suitable hydrophilic fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing a nonwettable, hydrophobic fiber with a hydrophilic polymer during or after the formation of the fiber.

For the purposes of the present invention, it is contemplated that selected blends of the various types of fibers mentioned above may also be employed. Moreover, the fiber selection may instead, or may additionally, include bicomponent or bi-constituent fibers that are hydrophilic or have been treated to be hydrophilic and are used to enhance the integrity and/or softness of the absorbent structure by bonding through heat activation.

It is also contemplated that the absorbent structure may instead, or may additionally, comprise hydrophobic fibers without departing from the scope of this invention. In another embodiment, the absorbent structure may comprise only a surface treated absorbent material, such as by forming the absorbent structure using conventional foaming techniques.

TABLE 3

| Superabsorbent Material | CATIOFAST VFH (Wt. %) | Swell Ratio | CRC (g/g) | Aul @ 0.9 psi (g/g) | Gel Stiffness Index | Free Swell GBP @ 0 psi ($\times 10^{-9}$ cm$^2$) | GPB under load @ 0.3 psi ($\times 10^{-9}$ cm$^2$) |
|---|---|---|---|---|---|---|---|
| SXM 9543 | 0 | 0 | 23.7 | 21.8 | 0.92 | 218 | 117 |
| | 2.5 | 2.5 | 21.4 | 19.7 | 0.92 | 2326 | 577 |

In one embodiment, an absorbent structure of the present invention comprises a non-woven web comprising hydrophilic fibers and the surface treated absorbent material made in accordance with the present invention. Examples of suitable hydrophilic fibers include naturally occurring organic fibers composed of intrinsically wettable material, such as cellulosic fibers. Suitable sources of cellulosic fibers include: wood fibers, such as bleached kraft softwood or hardwood, high-yield wood fibers, and ChemiThermoMechanical Pulp fibers; bagasse fibers; milkweed fluff fibers; wheat straw;

The absorbent structure may be formed in any conventional manner, such as by being air-formed, air-laid, co-formed, wet-laid, bonded-carded or formed by other known techniques in which fibers and absorbent materials are commingled to form a non-woven web. The absorbent structure can also be single layered or multiple layered in any shapes. The absorbent structure may also be a foam structure or it may be a laminate wherein the surface treated absorbent material is placed in a uniform or patterned array on at least one layer of permeable and hydrophilic fibers or web or between such layers.

The absorbent structure may be of substantially any shape and size suitable for its intended purpose. The absorbent structure may also comprise two or more non-woven webs or layers, which may be positioned in side-by-side relationship or surface-to-surface relationship, and all or a portion of adjacent webs or layers may be secured together to form the absorbent structure.

The surface treated absorbent material can be substantially homogeneously mixed with the hydrophilic fibers to provide a uniform distribution of the absorbent material and fibers throughout the absorbent structure. Alternatively, the surface treated absorbent material can be distributed non-uniformly within the absorbent structure, such as across the width, along the length and/or through the thickness of the structure to define discrete target regions or zones of the structure within which the absorbent material is distributed. The concentration of surface treated absorbent material within the absorbent structure can also be nonuniform through all or part of the thickness, across all or part of the width and/or along all or part of the length of the absorbent structure.

In general, the concentration of surface treated absorbent material within the absorbent structure is suitably about 90 weight percent or less based on the total weight of the absorbent structure, but is in any event greater than zero. In one embodiment, the concentration of surface treated absorbent material within the absorbent structure is suitably in the range of about 5 to about 90 weight percent, more suitably in the range of about 40 to about 90 weight percent and even more suitably in the range of about 40 to about 80 weight percent. In another embodiment the concentration of surface treated absorbent material within the absorbent structure is in the range of about 40 to about 60 weight percent.

The absorbent structure mayor may not be wrapped or otherwise encompassed by a suitable tissue or web wrap for maintaining the integrity and/or shape of the absorbent structure.

As described previously, the absorbent structure formed in accordance with the present invention may be incorporated in an absorbent article. As used herein, an absorbent article refers to an article which may be placed against or in proximity to the body of the wearer (e.g., contiguous to the body) to absorb and/or retain various waste discharged from the body. Some absorbent articles, such as disposable articles, are intended to be discarded after a limited period of use instead of being laundered or otherwise restored for reuse. In one embodiment, an absorbent article of the present invention comprises an outer cover, a bodyside liner positioned in facing relation with the outer cover and adapted for contiguous relationship with the body of the wearer, and an absorbent body disposed between the outer cover and the liner. The bodyside liner may be generally coextensive with the outer cover, or may instead overlie an area which is larger or smaller than the area of the outer cover, as desired.

In one embodiment, the outer cover is stretchable and mayor may not be somewhat elastic. More particularly, the outer cover is sufficiently extensible such that once stretched under the weight of the insulted absorbent body, the outer cover will not retract substantially back toward its original position. However, it is contemplated that the outer cover may instead be generally non-extensible and remain within the scope of this invention.

The outer cover may be a single layer structure or it may be a multi-layered laminate structure to provide desired levels of extensibility as well as liquid impermeability and vapor permeability. For example, the outer cover can be a two-layer construction, including an outer layer constructed of a vapor permeable material and an inner layer constructed of a liquid impermeable material, with the two layers being secured together by a suitable laminate adhesive or other bonding technique. The vapor permeable outer layer can be any suitable material and is desirably one which provides a generally cloth-like texture. Suitable materials for the outer layer include non-woven webs, woven materials, knitted materials and films. Nonwoven fabrics or webs have been formed from many known processes, for example, bonded carded web processes, meltblowing processes and spunbonding processes.

The liquid impermeable inner layer of the outer cover can be either vapor permeable (i.e., "breathable") or vapor impermeable. The inner layer is desirably manufactured from a thin plastic film, although other flexible liquid impermeable materials may also be used. More particularly, the inner layer can be made from either cast or blown film equipment, can be coextruded and can be embossed if so desired. It is understood that the inner layer may otherwise be made from any suitable non-elastic polymer composition and may include multiple layers. Where the inner layer is vapor permeable, it may contain such fillers as micropore developing fillers, e.g. calcium carbonate, opacifying agents, e.g. titanium dioxide; and antiblock additives, e.g. diatomaceous earth. Suitable polymers for the inner layer include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

The bodyside liner is suitably pliable, soft feeling, and nonirritating to the wearer's skin, and is employed to help isolate the wearer's skin from the absorbent body. The liner is desirably less hydrophilic than the absorbent body to present a relatively dry surface to the wearer, and is sufficiently porous to be liquid permeable to thereby permit liquid to readily penetrate through its thickness. A suitable bodyside liner may be manufactured from a wide selection of web materials. Various woven and nonwoven fabrics, including either or both synthetic and natural fibers, or film laminates, can be used for the liner. For example, the bodyside liner may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof. The bodyside liners may also be apertured to promote acquisition of fluid or to impart aesthetically pleasing patterns.

The various components of the absorbent article are assembled together using a suitable form of attachment, such as adhesive, sonic bonds, thermal bonds or combinations thereof. For example, in one embodiment the outer cover and absorbent body are secured to each other with lines of adhesive, such as a hot melt or pressure-sensitive adhesive. The bodyside liner is also secured to the outer cover and may also be secured to the absorbent body using the same forms of attachment.

In accordance with the present invention, the absorbent body comprises at least in part an absorbent structure as described previously herein. It is contemplated that the absorbent body may comprise one or more of the absorbent structures, such as in overlaid or side-by-side relationship, and/or it may comprise one or more layers in addition to the absorbent structure, such as a surge layer, without departing from the scope of this invention.

The various tests referred to previously herein are now described.

Free Swell Gel Bed Permeability Test

Figure 2:
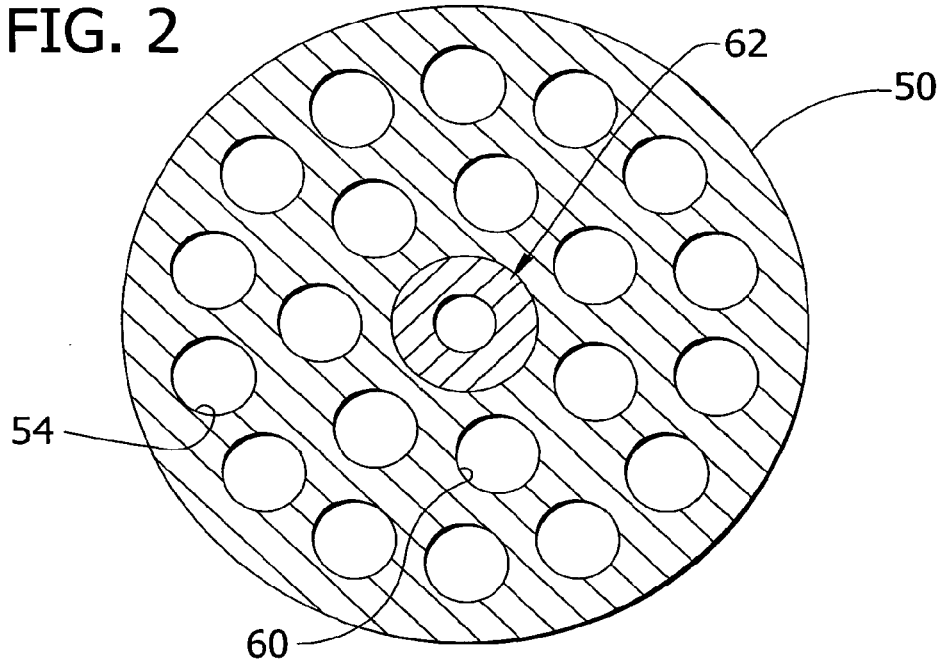
FIG. 2 is a section taken in the plane of line 2-2 of FIG. 1.

As used herein, the Free Swell Gel Bed Permeability (GBP) Test determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1 and 2 and indicated generally at 28. The test apparatus 28 comprises a sample container, generally indicated at 30, and a piston, generally indicated at 36. The piston 36 comprises a cylindrical LEXAN shaft 38 having a concentric cylindrical hole 40 bored down the longitudinal axis of the shaft. Both ends of the shaft 38 are machined to provide upper and lower ends respectively designated 42, 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 100 mesh stainless steel screen 64.

The sample container 30 comprises a cylinder 34 and a 400 mesh stainless steel cloth screen 66 that is biaxially stretched to tautness and attached to the lower end of the cylinder. A gel particle sample, indicated as 68 in FIG. 1, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 10 cm. Drainage holes (not shown) are formed in the sidewall of the cylinder 34 at a height of approximately 7.8 cm above the screen 66 to allow liquid to drain from the cylinder to thereby maintain a fluid level in the sample container at approximately 7.8 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is 0.9 weight percent sodium chloride solution in distilled water. The combined weight of the piston 36 and annular weight 48 equals approximately 596 grams (g), which corresponds to a pressure applied to the sample 68 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Gel Bed Permeability Test under "free swell" conditions, the piston 36, with the weight 48 seated thereon, is placed in an empty sample container 30 and the height is measured using a suitable gauge accurate to 0.01 mm with the platen removed. It is important to measure the height of each sample container 30 empty and to keep track of which piston 36 and weight 48 is used when using multiple test apparatus. The same piston 36 and weight 48 should be used for measurement when the sample 68 is later swollen following saturation.

The sample to be tested is prepared from particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Approximately 0.9 grams of the sample is placed in the sample container 30 and spread out evenly on the bottom of the sample container. The container, with 0.9 grams of sample in it, without the piston 36 and weight 48 therein, is then submerged in the test solution for a time period of about 60 minutes to saturate the sample and allow the sample to swell free of any restraining load.

At the end of this period, the piston 36 and weight 48 assembly is placed on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same thickness gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of test solution into the container is adjusted to maintain a fluid height of about 7.8 cm above the bottom of the sample container. The quantity of solution passing through the sample 68 versus time is measured gravimetrically. Data points are collected every second for at least twenty seconds once the fluid level has been stabilized to and maintained at about 7.8 cm in height. The flow rate Q through the swollen sample 68 is determined in units of grams/second (g/s) by a linear least-square fit of fluid passing through the sample 68 (in grams) versus time (in seconds).

Permeability in cm2 is obtained by the following equation:

$$K=[Q*H*\mu]/[A*\rho*P]$$

where K=Permeability (cm$^2$), Q=flow rate (g/sec), H=height of sample (cm), µ=liquid viscosity (poise) (approximately one centipoises for the test solution used with this Test), A=cross-sectional area for liquid flow (cm$^2$), ρ=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P=\rho * g * h$$

where ρ=liquid density (g/cm$^3$), g=gravitational acceleration, nominally 981 cm/sec$^2$, and h=fluid height, e.g., 7.8 cm for the Gel Bed Permeability Test described herein.

A minimum of three samples is tested and the results are averaged to determine the gel bed permeability of the sample.

Gel Bed Permeability Under Load Test

As used herein, the Gel Bed Permeability (GBP) Under Load Test, otherwise referred to herein as GBP at 0.3 psi, determines the permeability of a swollen bed of gel particles (e.g., the superabsorbent material or the absorbent material as those terms are used herein), under conditions that are commonly referred to as being "under load" conditions. The term "under load" means that swelling of the particles is restrained by a load generally consistent with normal usage loads applied to the particles, such as sitting, walking, twisting/etc. by the wearer.

More particularly, the Gel Bed Permeability Under Load Test is substantially the same as the Free Swell Gel Bed Permeability Test set forth previously with the following exception. After approximately 0.9 grams of the sample is placed in the sample container 30 and spread out evenly on the bottom of the sample container, the piston 36 and weight 48 are placed on the sample within the sample container prior to the sample container (with the piston and weight therein) being submerged in the test solution (0.9 wt % NaCl saline) for a time period of about 60 minutes. As a result, a 0.3 psi restraining load is applied to the sample as the sample becomes saturated and swells.

Absorbency Under Load Test

Figure 3:
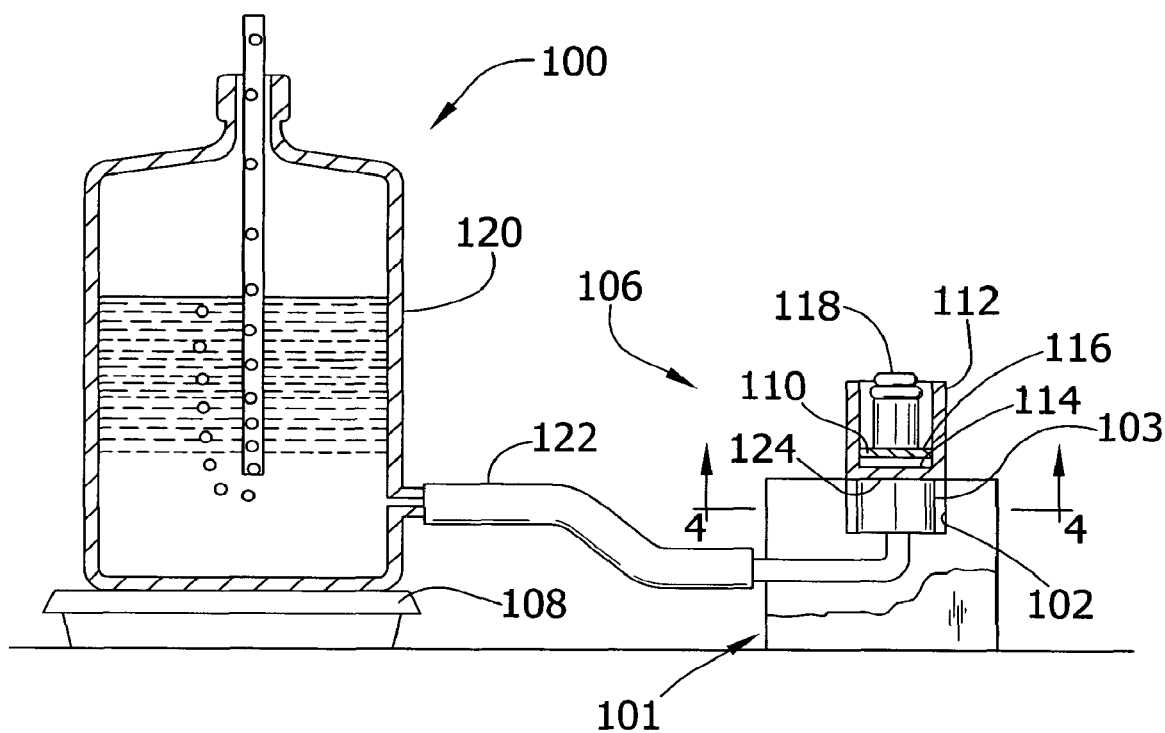
FIG. 3 is a cross-section of apparatus for conducting an Absorbency Under Load Test.

The Absorbency Under Load (AUL) Test measures the ability of the gel particle sample (e.g., such as the surface treated absorbent material or the superabsorbent material prior to being surface treated) to absorb a 0.9 weight percent solution of sodium chloride in distilled water at room temperature (test solution) while the material is under a 0.9 psi load. Apparatus 106 for conducting the AUL Test is shown in FIG. 3 and comprises a Demand Absorbency Tester (DAT), generally indicated at 100, which is similar to the Gravimetric Absorbency Test System (GATS) available from M/K Systems of Danners, Mass., U.S.A., and to the system described by Lichstein at pages 129-142 of the INDA Technological Symposium Proceedings, March 1974.

Figure 4:
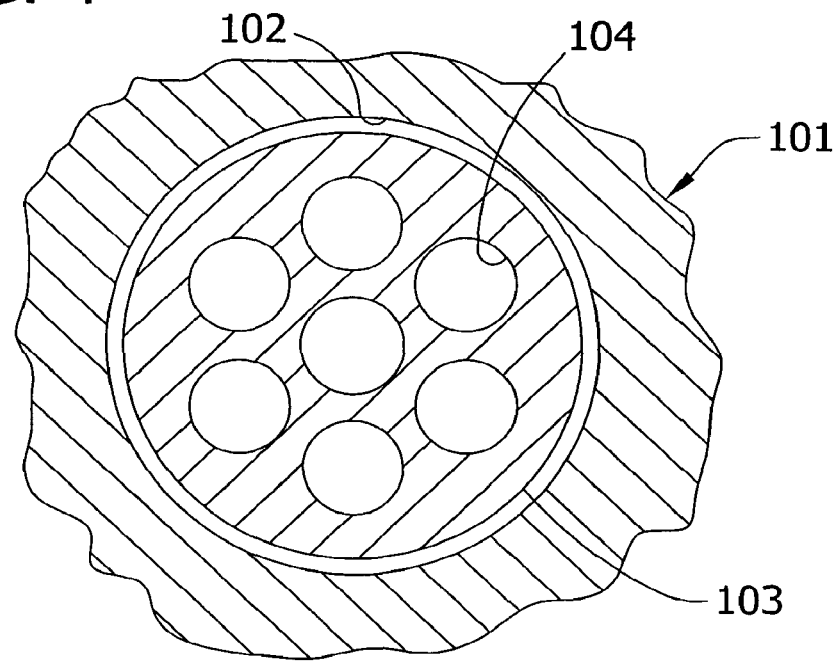
FIG. 4 is a section taken in the plane of line 4-4 of FIG. 3.

The test apparatus further comprises a test stand, generally indicated at 101 (FIG. 4) having a cavity 102 formed therein and a porous plate 103 seated in the cavity and having a central porous area of about 2.54 cm diameter formed by a plurality of bores 104 extending through the plate. The cavity 102 shown in FIG. 4 has a diameter of about 3.2 cm and the porous plate 103 has a diameter of about 3.1 cm and comprises seven bores 104, each having a diameter of about 0.3 cm. One of the bores 104 is centrally located and the remaining six bores are concentrically positioned about the central bore with the spacing from the center of the central bore to the center of each adjacent bore is about one centimeter.

A sample container for containing a sample 110 to be tested comprises a cylinder 112 and a stainless steel cloth screen 114 that is biaxially stretched to tautness and attached to the lower end of the cylinder. The cylinder 112 may be bored from a transparent LEXAN rod or equivalent material, or it may be cut from a LEXAN tubing or equivalent material, and has an inner diameter of about one inch (about 2.54 cm). The stainless steel cloth screen 114 is suitably a 100 mesh screen A disc, or piston 116 is machined from a LEXAN rod, Plexiglass or equivalent material and has a diameter sized such that it fits within the cylinder 112 with minimum wall clearance but still slides freely. The height of the piston 116 is approximately 0.8 cm and the weight of the piston is suitably about 4.4 grams to provide a load over the cross-sectional area of the sample in the container of about 0.01 psi. A weight 118 is sized (e.g., having a diameter of about 2.5 cm) for seating on the piston 116 to increase the load (e.g., in addition to the weight of the piston) on the sample. For example, a weight of about 317 grams is used to provide a load (e.g., including the piston weight) of about 0.9 psi over the cross-sectional area of the sample in the container.

The cavity 102, and hence the porous plate 103, is in fluid communication with a reservoir 120 containing test solution (0.9 weight percent sodium chloride solution in distilled water at room temperature) via a suitable conduit 122. As shown in FIG. 3, the reservoir 120 is seated on an electrostatic balance 108.

A sample 110 of gel particles weighing about 0.160 grams is prepared by screening the particles through a U.S. standard 30 mesh screen and retaining the particles on a U.S. standard 50 mesh screen so that the sample comprises particles in the size range of about 300 to about 600 microns. The sample is weighed on suitable weighing paper and then loaded into the sample container (with the piston 116 removed) so that the particles are uniformly distributed and uniformly distributed and overlay the screen at the bottom of the container. The sample container is gently tapped to level the bed of particles in the container.

The AUL Test is initiated by placing a circular piece of GF/A glass filter paper 124 onto the porous plate 103 over the bores 104 formed therein and allowing to become saturated by test solution delivered from the reservoir 120 to the porous plate via the conduit 122. The paper 124 is suitably sized larger than the inner diameter of the cylinder 112 and smaller than the outer diameter thereof to ensure good contact while inhibiting evaporation over the bores 104. The electrostatic balance 108 is zeroed at this time. The piston 116 and weight 118 are placed on the sample within the container and the container (with the sample, piston and weight therein) is placed on the plate 103 over the saturated glass filter paper 124 to allow test solution to be taken into the sample in the container via the conduit 122, bores 104 in the plate 102 and the filter paper.

The electrostatic balance 108 is used to measure the flow of test solution to the sample over a period of about 60 minutes. The amount (in grams) of solution taken into the sample after about 60 minutes divided by the dry weight of the sample (e.g., about 0.160 grams) is the AUL value of the sample in grams of liquid per gram weight of sample.

Two checks can be made to ensure the accuracy of the measurement. First, the height the piston 116 rises above the screen 114 at the bottom of the sample container multiplied by the cross-sectional area of the piston should roughly equal the amount of solution picked up by the sample over the 60 minute period. Second, the sample container can be weighed before (e.g., while the superabsorbent material is dry) and after the test and the difference in weight should roughly equal the amount of solution picked up by the sample over the 60 minute period.

A minimum of three tests is performed and the results are averaged to determine the AUL value at 0.9 psi. The samples are tested at 23±1 degrees Celsius at 50±2 percent relative humidity.

Centrifuge Retention Capacity Test

The Centrifuge Retention Capacity (CRC) Test measures the ability of the gel particles (e.g., such as the surface treated absorbent material or the superabsorbent material prior to being surface treated) to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{\text{sample/bag weight after centrifuge} - \text{empty bag weight after centrifuge} - \text{dry sample weight}}{\text{dry sample weight}}$$

The three samples are tested and the results are averaged to determine the centrifuge retention capacity (CRC). The samples are tested at 23±1 degrees Celsius at 50±2 percent relative humidity.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

What is claimed is:

1. An absorbent material consisting essentially of a superabsorbent polymer consisting of
   a) at least about 75% by weight of the superabsorbent polymer of an anionic polymer comprising functional groups selected from carboxyl groups, sulfonate groups, sulphate groups, sulfite groups, and phosphate groups; and
   b) an internal crosslinking agent based on the polymerizable unsaturated acid group containing monomer, wherein the superabsorbent polymer has a degree of neutralization of greater than about 25%; wherein elements a) and b) are polymerized and prepared into superabsorbent polymer particles and further comprising the following surface additives to form surface treated superabsorbent polymer particles
      i) from about 0.5% to about 5% by weight of surface crosslinking agent based on the superabsorbent polymer composition; and
      ii) from about 0.63% to about 5% by weight of a non-cross linked cationic polymeric coating based on the superabsorbent polymer composition;
   said absorbent material having a centrifuge retention capacity as determined by a Centrifuge Retention Capacity Test of at least about 20 g/g and a gel bed permeability under load as determined by a Gel Bed Permeability Under Load Test of at least about $300 \times 10^{-9}$ cm$^2$.

2. The absorbent material of claim 1 wherein the absorbent material has a gel bed permeability under load as determined by the Gel Bed Permeability Under Load Test of at least about $400\times10^{-9}$ cm$^2$.

3. The absorbent material of claim 1 wherein the absorbent material has a centrifuge retention capacity as determined by a Centrifuge Retention Capacity Test of at least about 25 g/g.

4. The absorbent material of claim 1 wherein the absorbent material has a free swell gel bed permeability as determined by a Free Swell Gel Bed Permeability Test of at least about $2,000\times10^{-9}$ cm$^2$.

5. The absorbent material of claim 4 wherein the absorbent material has a free swell gel bed permeability as determined by the Free Swell Gel Bed Permeability Test of at least about $3,000\times10^{-9}$ cm$^2$.

6. The absorbent material of claim 4 wherein the absorbent material has a free swell gel bed permeability as determined by the Free Swell Gel Bed Permeability Test of at least about $2,500\times10^{-9}$ cm$^2$.

7. The absorbent material of claim 1 wherein the superabsorbent polymer comprises at least about 85% by weight of an anionic polymer.

* * * * *